US006432038B1

(12) United States Patent
Bakane

(10) Patent No.: US 6,432,038 B1
(45) Date of Patent: Aug. 13, 2002

(54) ARTIFICIAL URINARY SPHINCTER

(76) Inventor: Ramesh Bakane, 2030 W. Lola Dr., Marion, IN (US) 46952

( * ) Notice: Subject to any disclaimer, the term of this patent is extended or adjusted under 35 U.S.C. 154(b) by 22 days.

(21) Appl. No.: 09/783,327

(22) Filed: Feb. 15, 2001

(51) Int. Cl.⁷ .............................. A61F 2/00; A61F 2/08
(52) U.S. Cl. ..................................... 600/29; 623/14.13
(58) Field of Search ................... 600/29–31; 623/1.24, 623/14.13; 128/885, 899; 242/371

(56) References Cited

U.S. PATENT DOCUMENTS

| 3,679,317 | A | | 7/1972 | Larson |
| 3,810,256 | A | | 5/1974 | Summers |
| 4,118,805 | A | | 10/1978 | Reimels |
| 4,222,377 | A | * | 9/1980 | Burton .......................... 600/31 |
| 4,571,749 | A | | 2/1986 | Fischell |
| 4,705,518 | A | * | 11/1987 | Baker et al. ................. 128/899 |
| 4,731,083 | A | * | 3/1988 | Fischell .................... 623/14.13 |
| 4,784,660 | A | | 11/1988 | Fischell |
| 5,041,136 | A | * | 8/1991 | Wascher et al. .............. 600/30 |
| 5,078,676 | A | * | 1/1992 | Bailly .......................... 600/31 |
| 5,088,980 | A | * | 2/1992 | Leighton ...................... 600/30 |
| 5,520,606 | A | * | 5/1996 | Schoolman et al. ......... 128/885 |
| 5,562,598 | A | | 10/1996 | Whalen et al. |
| 5,634,878 | A | * | 6/1997 | Grundei et al. ............... 600/30 |
| 5,643,194 | A | | 7/1997 | Negre |
| 5,954,766 | A | * | 9/1999 | Zadno-Azizi et al. ...... 623/1.24 |
| 6,022,312 | A | * | 2/2000 | Chaussy et al. .............. 600/29 |
| 6,063,119 | A | | 5/2000 | Pintauro et al. |
| 6,074,341 | A | | 6/2000 | Anderson et al. |
| 6,095,969 | A | | 8/2000 | Karram et al. |
| 6,149,667 | A | * | 11/2000 | Hovland et al. ............... 600/29 |

FOREIGN PATENT DOCUMENTS

FR 2769491 A1 * 4/1999 ............. A61F/2/00

* cited by examiner

Primary Examiner—Eric F. Winakur
Assistant Examiner—Nikita Veniaminov
(74) Attorney, Agent, or Firm—Richard C. Litman

(57) ABSTRACT

An artificial urinary sphincter operable as a single, uncomplicated component, not prone to failure, and easily repaired. Being preassembled, installation is easy through a single incision in one site. It incorporates an outer cuff having an inner cuff of interconnecting flexible fluid-containing portions. The outer cuff overlaps itself where a spring loaded push button device is installed. The device acts like a retractable ball point pen, pushing on the overlapped portion to compress the fluid-containing portions, to compress and shut the urethra when the push button is first pushed, and then alternately relaxing pressure on the overlapped portion so as to release pressure on the urethra upon additional pushing. Circumferential wires on pulleys mounted on an inner portion of the button alternately contract and relax radially inward pressure on the inner cuff, coordinated with inward pressure and relaxation of overlapped outer cuff portion.

14 Claims, 13 Drawing Sheets

ARTIFICIAL URINARY SPHINCTER

BACKGROUND OF THE INVENTION

1. Field of the Invention

The present invention relates to medical devices. More particularly, the present invention relates to mechanical implants acting as urinary sphincters in human beings having urinary incontinence.

2. Description of the Related Art

Currently available urinary sphincter devices are multi-component and cumbersome to place surgically in the human body. Multiple components need to be installed in different locations, and this is a time consuming and difficult process. Malfunctions in these devices are generally very difficult to detect and correct. They have very complicated components, making assembly, difficult and prone to complications. Those devices which use an inflatable ring to close off the urethra are prone to non-uniform inflation and resultant injury to the urethra. Others may not be effective for severe incontinence, or require access through the skin to operate. Some employ a magnetically operated valve requiring an external magnetic key to operate, the key being subject to loss or misplacement. Devices inserted directly into the urethra increase the likelihood of infection. Likely failure modes in many devices leave the urethra closed, which would result in the need of timely surgery to avoid bladder damage.

U.S. Pat. No. 3,810,259, issued May 14, 1974, to Summers is complicated and intrusive, and requires the use of magnetic keys which are subject to loss, or may be otherwise unavailable.

U.S. Pat. No. 5,643,194, issued Jul. 1, 1997, to Negre is similarly subject to loss of the very specialized magnetic key, and is primarily directed toward relief and drainage of fluid for treatment of hydrocephalus. This device could not be used to control urinary incontinence where a urethra remains intact.

U.S. Pat. No. 4,571,749, issued Feb. 25, 1986, and U.S. Pat. No. 4,784,660, issued Nov. 15, 1988, both to Fischell, describe inflatable cuffs located around the urethra. These devices are not uniformly inflated, resulting in likely damage to the urethra.

U.S. Pat. No. 4,118,805, issued Oct. 10, 1978, to Reimelds describes an artificial sphincter. It is a very complicated device, and thus can be subject to failure or maladjustment.

U.S. Pat. No. 6,074,341, issued Jun. 13, 2000, to Anderson et al. describes mechanically complicated embodiments of an artificial urethra sphincter. The mechanical operation of the occlusive apparatus appears to be difficult to operate through the skin. Other means of operation are complicated and subject to failure.

U.S. Pat. No. 6,095,969, issued Aug. 1, 2000, to Karram et al. describes an implantable device for controlling stress incontinence in female patients. This device is intended to control incontinence when a patient is coughing, etc. It would not be effective in more severe cases of incontinence.

U.S. Pat. No. 6,063,119, issued May 16, 2000, to Pintauro et al. describes a device for maintaining urinary incontinence. The device is inserted into the urethra and partially into the bladder. Such a device enhances the likelihood of infections and may potentially cause damage to the urethra inner wall or bladder.

None of the above inventions and patents, taken either singularly or in combination, is seen to describe the instant invention as claimed. Thus, an artificial urinary sphincter solving the aforementioned problems is desired.

SUMMARY OF THE INVENTION

The present invention provides a device for treatment of urinary incontinence in males and females which is a single component, mechanically uncomplicated, and hence less prone to failure. Malfunctions are easily fixed. Since it will be preassembled, it is easy to install through a single incision in one site.

The device incorporates an outer cuff having an inner cuff of interconnecting flexible fluid-containing portions. The outer cuff is installed. The device acts much as that of a retractable ball point pen, pushing on the overlapped portion to compress the fluid-containing portions so as to compress and shut the urethra when the button is first pushed, and then alternately relaxing pressure on the overlapped portion so as to release pressure on the urethra upon pushing the button the second time.

The fluid-containing portions are so designed that they will expand concentrically toward the urethra. Wires are wrapped around pulleys mounted on an inner portion of the push button base and one end of each wire anchored to the outer cuff in the vicinity of its overlapping outer portion, so as to move inward when the push button of the push button assembly is pushed. The wires wrap around the inner cuff of the artificial sphincter and are mounted at their other end to the outer cuff near its fixation opening so as to alternately contract and relax circumferential pressure on the inner cuff. This contracting action is coordinated with the inward pressure and relaxation of the overlapped outer cuff portion.

Accordingly, it is a principal object of the invention to provide an artificial urinary sphincter which is simple in design, easily used, and requires only one incision to implant.

It is another object of the invention to provide an artificial urinary sphincter as above providing uniform pressure around the urethra in a closed position.

It is a further object of the invention to provide an artificial urinary sphincter as above having an outer cuff surrounding an inner cuff, the inner cuff having interconnecting fluid filled compartments for providing uniform pressure around the urethra.

Still another object of the invention is to provide an artificial urinary sphincter having an assembly operable by a push button operated through the skin which alternately opens and closes the urinary sphincter.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
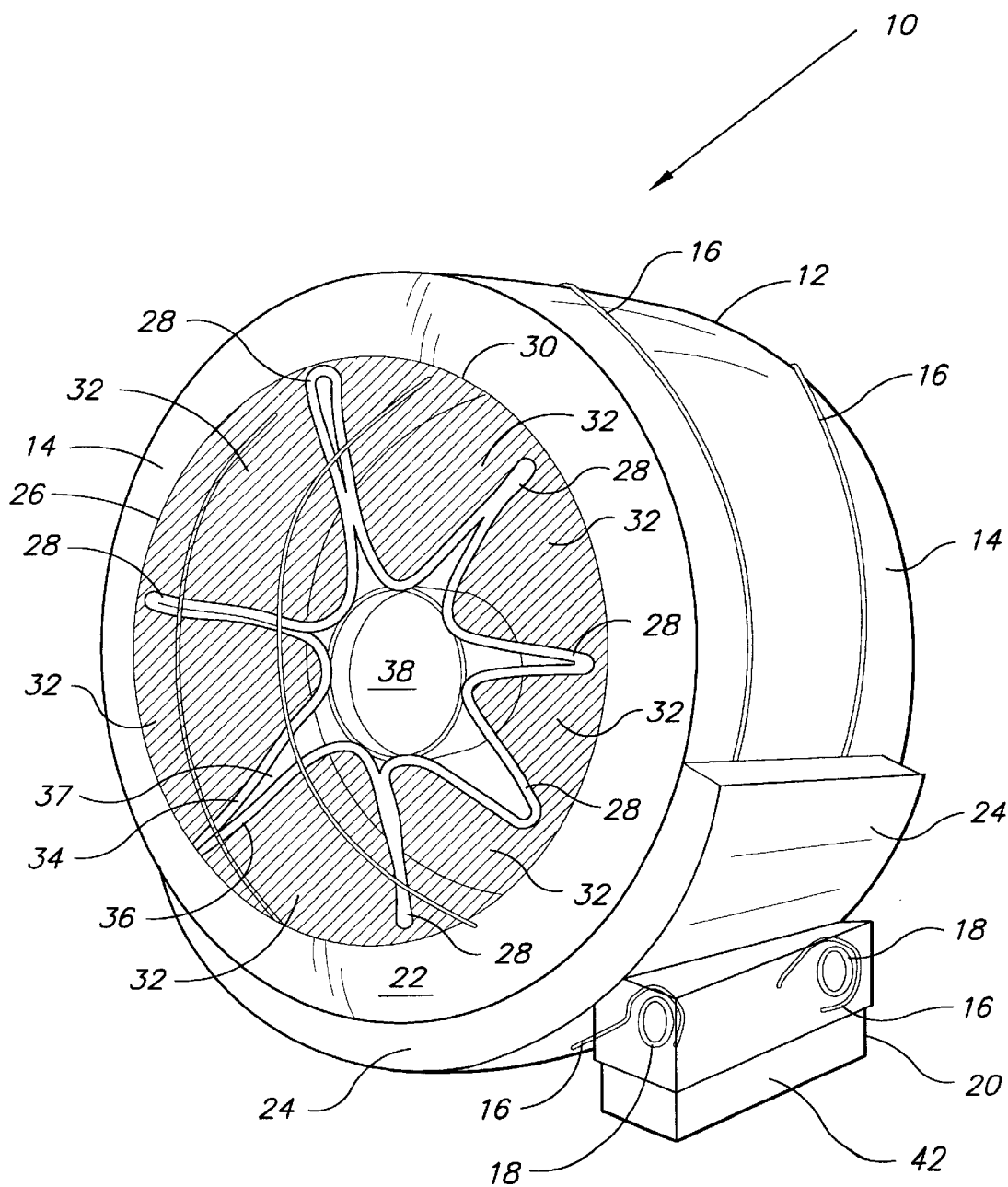
FIG. 1 is a diagrammatical perspective view of one embodiment of the artificial urinary sphincter of the present invention.

Referring to FIG. 1, the artificial urinary sphincter system 10 comprises artificial sphincter 12 having outer cuff 14. Circumferential wires 16 run over pulleys 18 and are attached at push button assembly 20. Push button assembly 20, having push button 42, is located and attached to the outer overlap portion 24 of outer cuff 14. Inner overlap portion 22 is slidingly engaged with outer overlap portion 24.

Outer cuff 14 surrounds inner cuff 26 having interconnecting fluid-containing cuff chambers 32 partially separated from each other by inner cuff walls 28, and the fluid therein is free to flow through the clearance between inner cuff walls 28 and inner cuff outer wall 30.

Inner cuff chambers 32 begin with inner cuff inner chamber wall 36 and end with inner cuff outer chamber wall 34, thereby defining inner cuff void space 37 which allows the inner cuff to slide around the urethra upon implant. Inner cuff chambers 32 extend radially inward toward urethra 38 to a closed position when contracting pressure is placed on outer cuff 14 by placing tension on wires 16 by pushing push button 42 of assembly 20.

Push button assembly 20 contains a retractable device similar to that of a retractable ball point pen.(not shown) Upon pushing push button 42 again, tension on wires 16 is relaxed, allowing the inner cuff chambers to radially retract to the open position.

Figure 2:
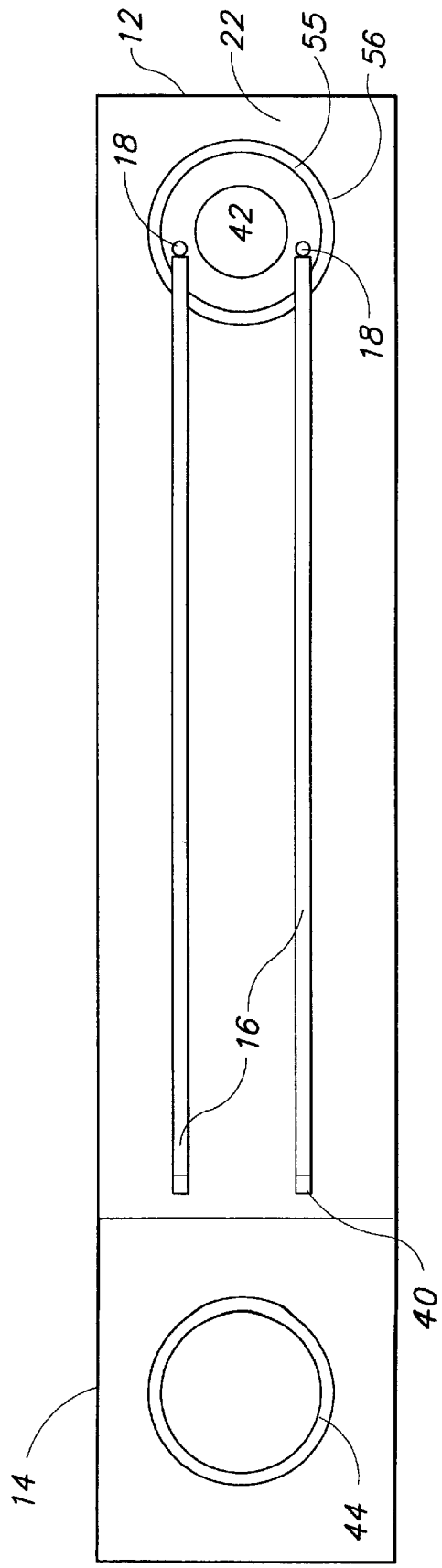
FIG. 2 is diagrammatical elevational view of another embodiment of the artificial urinary sphincter of the present invention illustrating the outer casing in an open position for installation on the urethra.

Referring to FIG. 2, there is shown a diagrammatical side view in elevation of artificial sphincter 12 without inner cuff 26 (see FIG. 3) before it is installed around the urethra. The overlapping outer portion of outer cuff 14 defines a fixation opening 44 which is drawn around inner overlap portion 22 and placed over push button 42, and push button base 56 of push button assembly 20 (see FIG. 3). to be fixed in groove 55 of push button base 56. Wire cavities 40 are provided for wires 16 to anchor to outer casing overlap portion near fixation opening 44. The push button 42 may be rectangular and normal to the outer cuff as shown in FIG. 1, above, with base 56 conforming thereto, or push button 42 may be circular as shown in FIG. 2 with base 56 conforming thereto.

Figure 3:
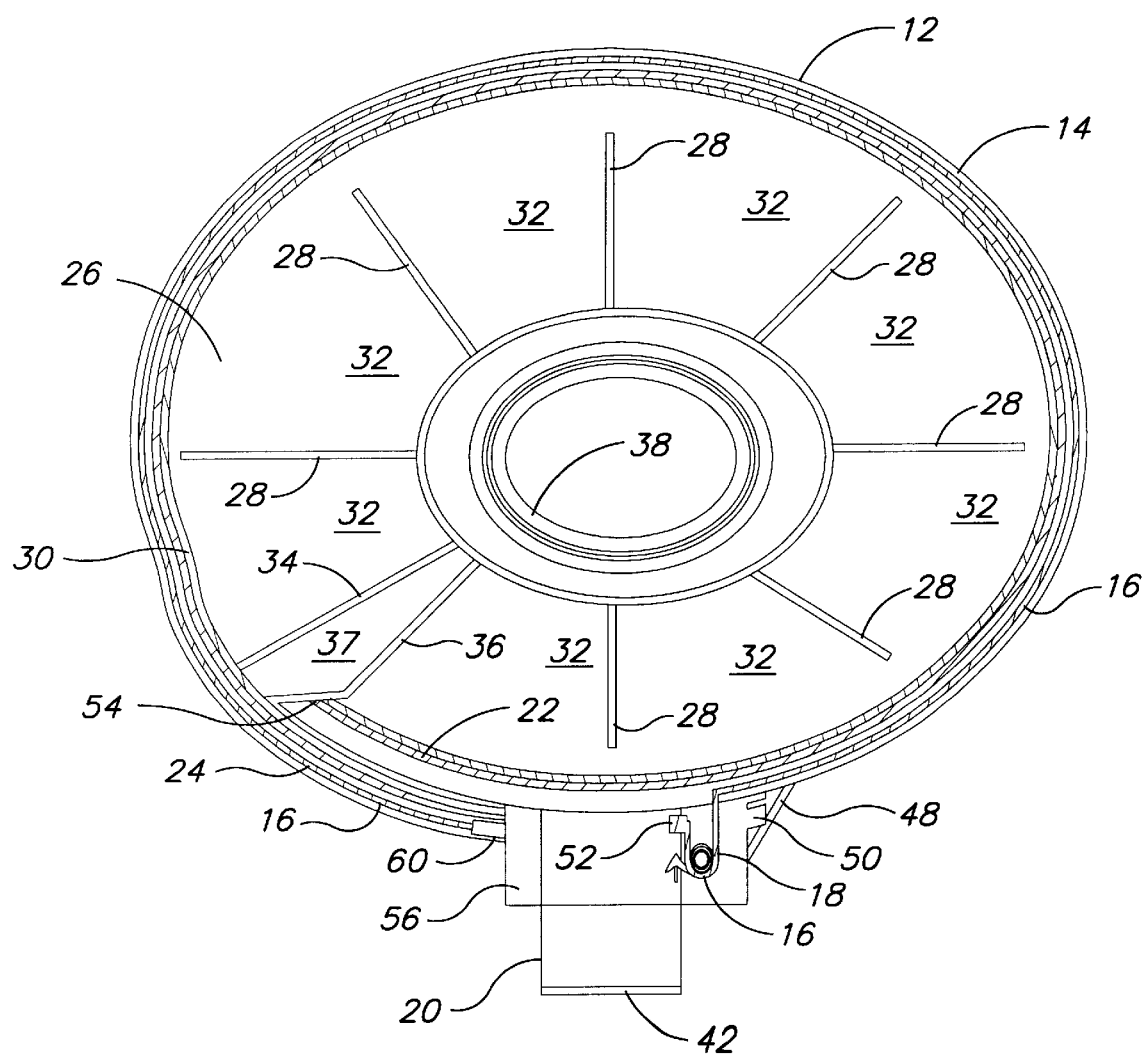
FIG. 3 is diagrammatical plan view of the urinary sphincter of FIG. 2, as it surrounds a section of a urethra in an open position.

Referring to FIG. 3, there is shown a diagrammatical plan view of the artificial sphincter 12 in an open position as it surrounds a section of a urethra 38. Outer sphincter cuff 14 extends from an outer end 50 through outer overlap portion 24, around interconnecting fluid-containing inner cuff 26, through inner overlap portion 22, and ends at inner end 54. The portion of outer overlap portion 24 which surrounds push button assembly 20 is broken away for illustration purposes.

Push button base to outer cuff connector 48 attaches push button assembly 20 to outer cuff 14 to maintain connection during installation of the artificial sphincter, and may be made of an extensible material such as rubber to allow relative motion between outer cuff 14 and push button base 56. Fluid-containing inner cuff 26 features inner cuff walls 28 extending radially outward from urethra 38 and ending near inner cuff outer wall 30, forming inner cuff chambers 32. Inner cuff walls 28 allow fluid to travel around between the partial walls 28 and inner cuff outer wall 30, forming interconnected inner cuff chambers 32. A gap 37 in interconnecting fluid-containing inner cuff 26 is formed between inner cuff outer chamber wall 34 and inner cuff inner chamber wall 36 so as to allow outer cuff outer overlap portion 24 and outer cuff inner overlap portion 22 to overlap.

Outer cuff 14 has no inner cuff chambers 32 in the outer overlap portion 24 ending in outer cuff outer end 50. Push button assembly 20 bears radially inward upon outer cuff 14 at its inner overlap portion 22 near inner end 54. Pulleys 18 are located in and attached to the inner wall of push button base 56 and direct circumferential wires 16 to push button assembly 20, they being secured at circumferential wire attachment points 52 within push button assembly 20. The wires then run around the inner cuff 26 and the opposite ends of wires 16 are threaded through cavities 40 (see FIG. 2) and anchored to outer cuff 14 near push button base 56 at remote attachment points 60.

Figure 4:
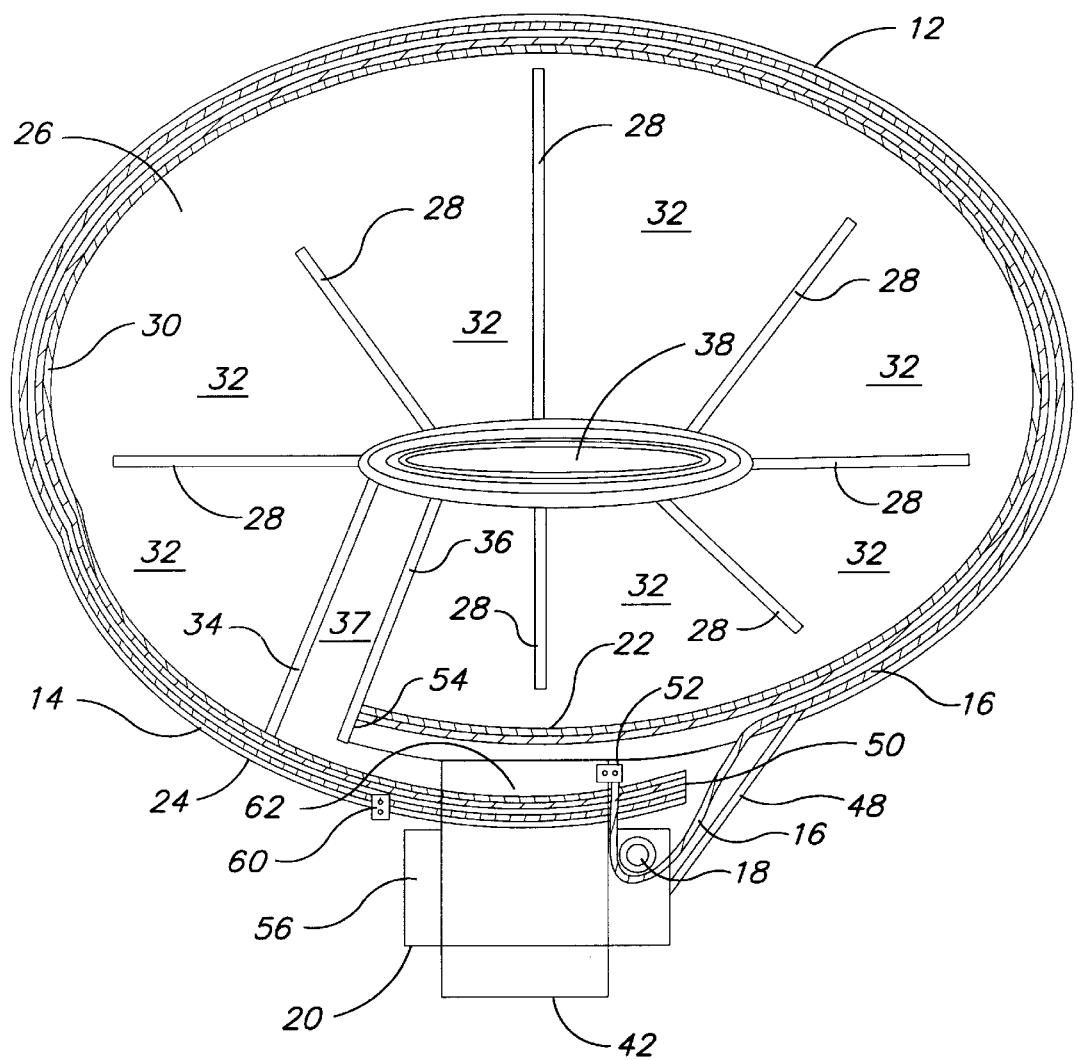
FIG. 4 is a diagrammatical plan view of the urinary sphincter of FIG. 2, as it surrounds a section of a urethra in a closed position.

Referring to FIG. 4, there is shown a diagrammatical plan view of the artificial sphincter 12 similar to that of FIG. 3, but in the open position. In practice, outer overlap portion 24 overlays portions of push button assembly 20 and wires 16, shown here for illustrative purposes. Push button assembly 20 has engaged the inner overlap portion 22 of the outer cuff 14, moving it inward relative to the outer overlap portion 24 of outer cuff 14. Also, circumferential wires 16 are tightened around outer cuff 14 by running over pulleys 18 as the inner push rod 62 of closure assembly 48 (see FIG. 5) is pushed inward as push button 42 is pushed inward. Pulleys 18 remain fixed within push button base 56 relative to the inward movement of the inner end portion of push button assembly 20. These two operations act to distribute inward radial force on interconnecting fluid-containing cuff chambers 32, resulting in an inward pressure causing the centrally located urethra 38 to close.

Figure 5:
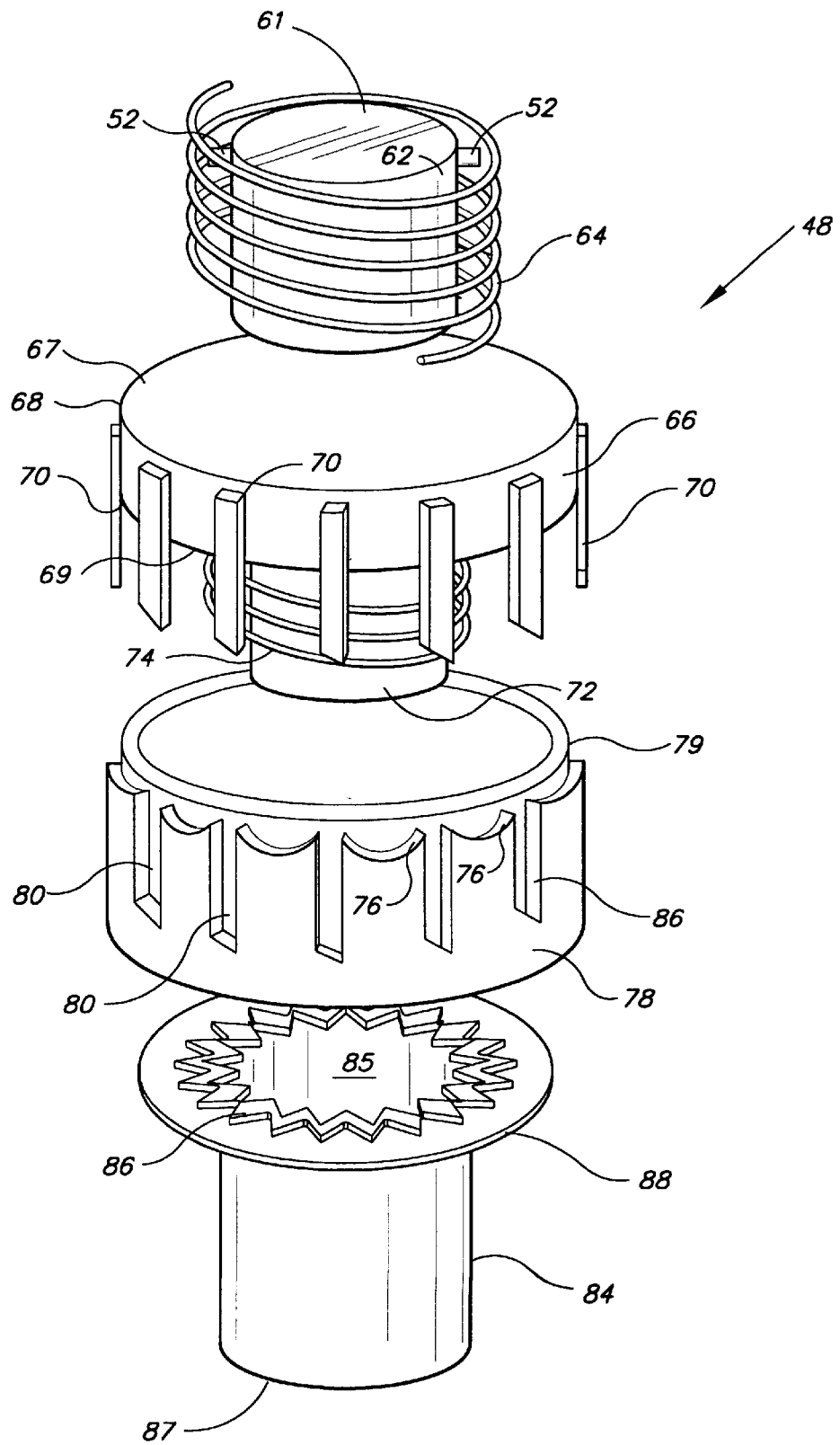
FIG. 5 is a diagrammatical exploded view in perspective of the closure assembly of FIGS. 3 and 4.

Referring to FIG. 5, there is shown a diagrammatical exploded view in perspective of closure assembly 48 of push button assembly 20 (see FIG. 4). Assembly 48 is a combination of elements which cooperate to simulate the spring-loaded action of a ball point pen that alternately extends and retracts the refill portion of the pen. The major components of push button assembly 20 are solid cylindrical inner push rod 62, generally cylindrical rotating locker 66, hollow cylindrical push button assembly casing 78, and hollow cylindrical outer push rod 84. Rotating locker 66 is generally cylindrical in shape, having an inner portion 68 having inner end 67. Rotating locker inner portion 68 is of such diameter that spaced rotating locker teeth 70, directed outward, lengthwise and distributed around the circumference of inner portion 68, interact with outer wall 79 of push button casing 78. Spaced rotating locker teeth 70 each have angled end portions ending in a sharp point. Rotating locker outer portion 72 has a second diameter smaller than the diameter of inner portion 68, forming an intermediate wall 69, normal to the central axis of rotating locker 66.

Outer rotating locker coil spring 74 is located along rotating locker outer portion 72 and bears against intermediate wall 69 at its inner end, and outer push rod 84 at its outer end. Push button casing 78 is cylindrical in conformation, its outer wall 79 featuring generally crosswise, spaced, locking ridges 76 and lengthwise grooves 80, defined thereby, which alternately interact with spaced rotating locker teeth 70 as artificial sphincter 12 (see FIG. 1) is opened and closed by actuation of push button assembly 20 (see FIG. 4). Inner push rod 62 bears against rotating locker 66 at locker inner end 67 and against outer cuff 14 (see FIG. 3) at a point in its inner overlap portion 22. Inner push rod coil spring 64 surrounds inner push rod 62 and bears against rotating locker inner end 67 and inner overlap portion 22 of outer cuff 14. Wire attachment points 52 are located near the inner end of inner push rod 62. Outer push rod 84 has a solid outer end 87 and features teeth 88 disposed around hollow core 85 at its inner end, and outer push rod collar 88 to seal outer push rod 84 within casing 78.

Figure 6:
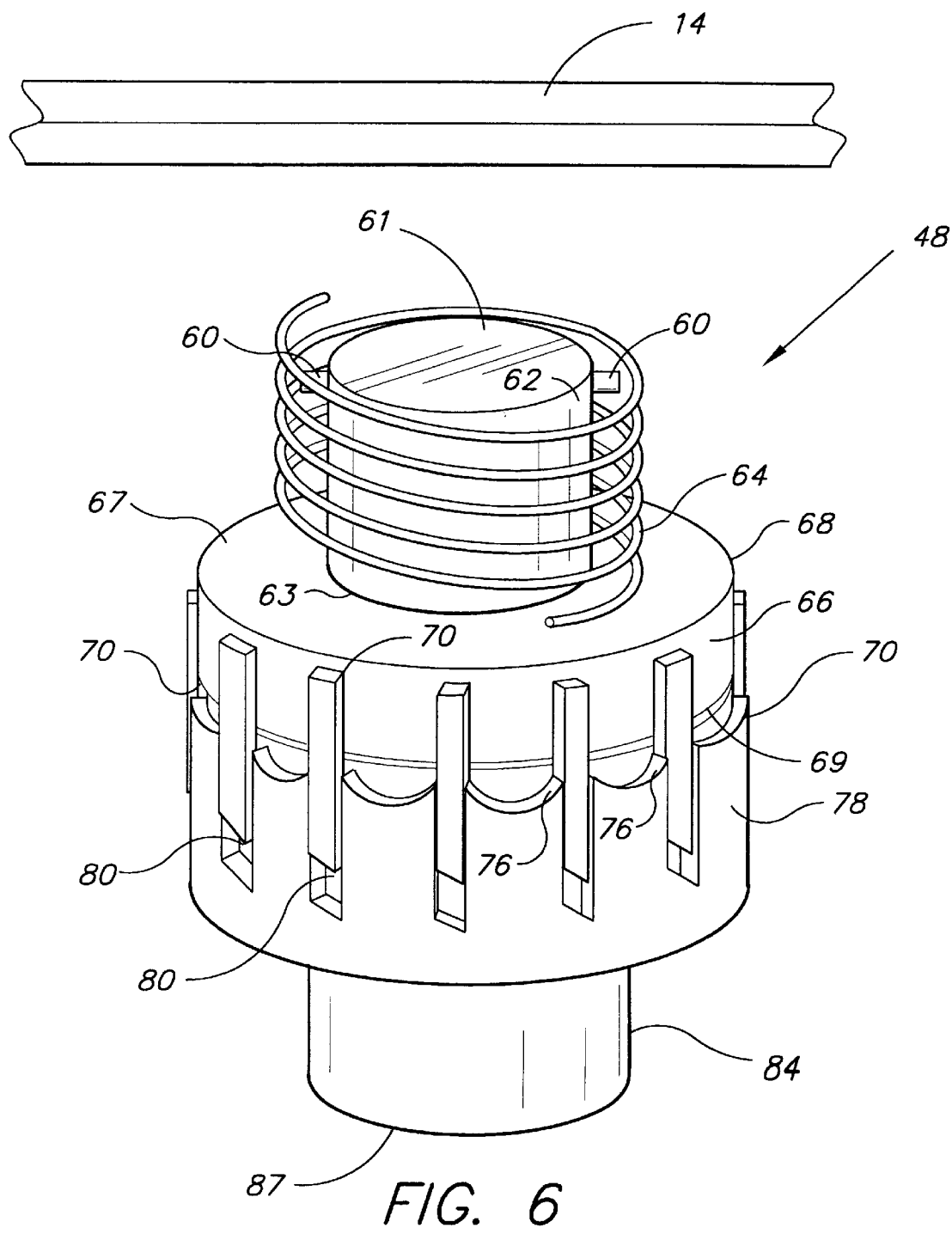
FIG. 6 is a diagrammatical perspective view of the closure assembly of FIG. 5 as assembled in the open position.
Figure 7:
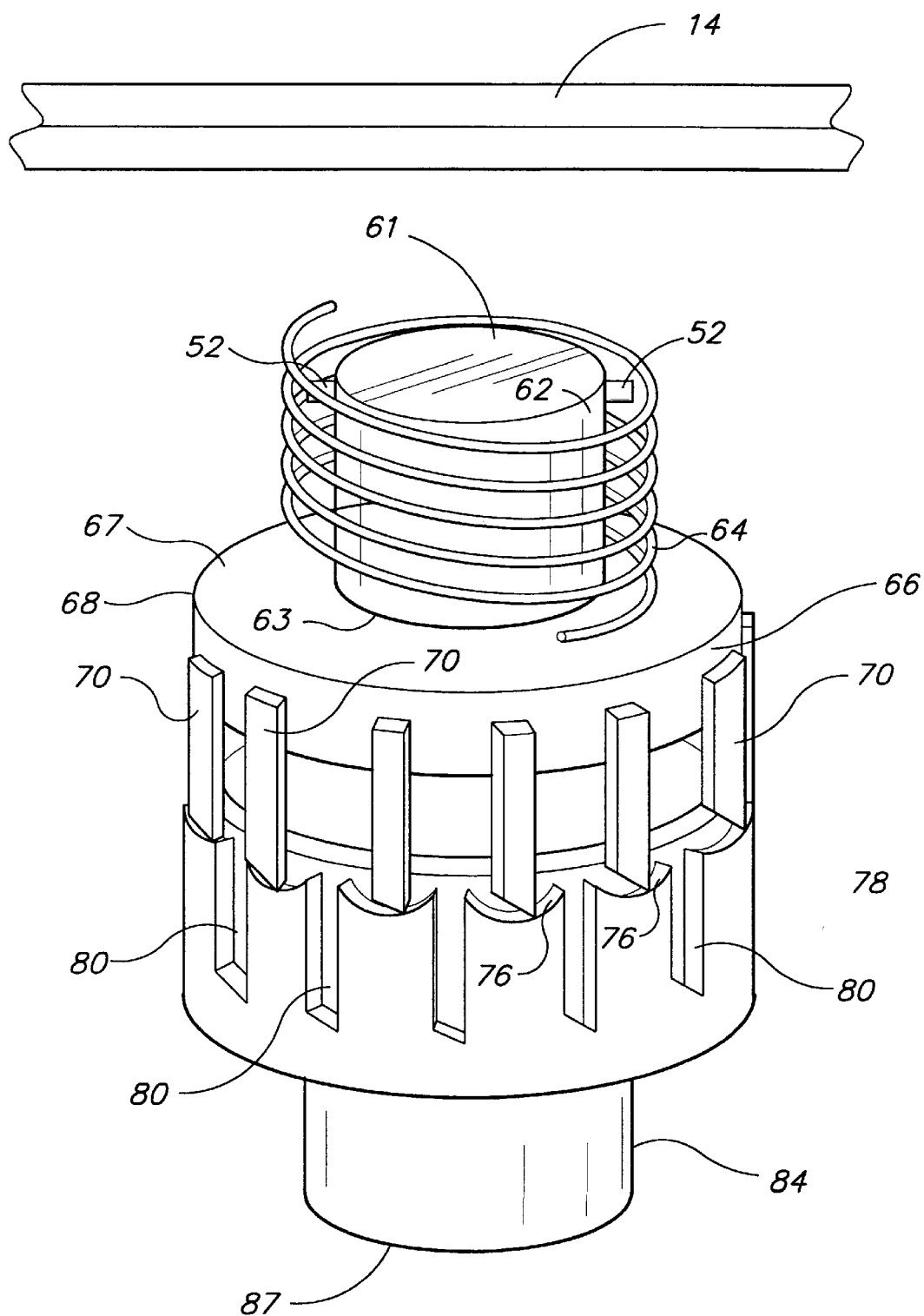
FIG. 7 is a diagrammatical perspective view of the closure assembly of FIG. 6 in the closed position.

Referring to FIGS. 6 and 7, there are shown the assembled closure assembly 48 of FIG. 5 in its respective open and closed position. A portion of outer cuff 14 is shown spaced from the closure assembly 48 for illustrative purposes, but bears against the closure assembly in use. As diagrammatically illustrated in FIG. 6, closure assembly outer push rod 84 hangs loosely within closure assembly casing 78, and is held therein by outer push rod teeth 86 resting on outer push rod cuff 88 (see FIG. 5). Inner push rod 62 does not exert force on outer cuff 14 in the open position. Rotating locker teeth 70 are aligned with casing grooves 80 and inserted therein by the action of inner push rod spring 64.

As diagrammatically illustrated in FIG. 7, push button closure assembly inner push rod 62 bears against the inner overlap portion 22 of outer cuff 14 (see FIG. 3) at inner end 61 and against inner end 67 of rotating locker 67 at inner push rod outer end 63, while the outer end portion 72 (see FIG. 5)of rotating locker 66 is held within the hollow core 85 of outer push rod 84. Rotating locker spaced teeth 70 rest on casing locking ridges 76, and inner push rod 62 is forced inward by rotating locker 66 at inner end 67, transferring force to outer cuff 14, thus, closing the sphincter.

Figure 8:
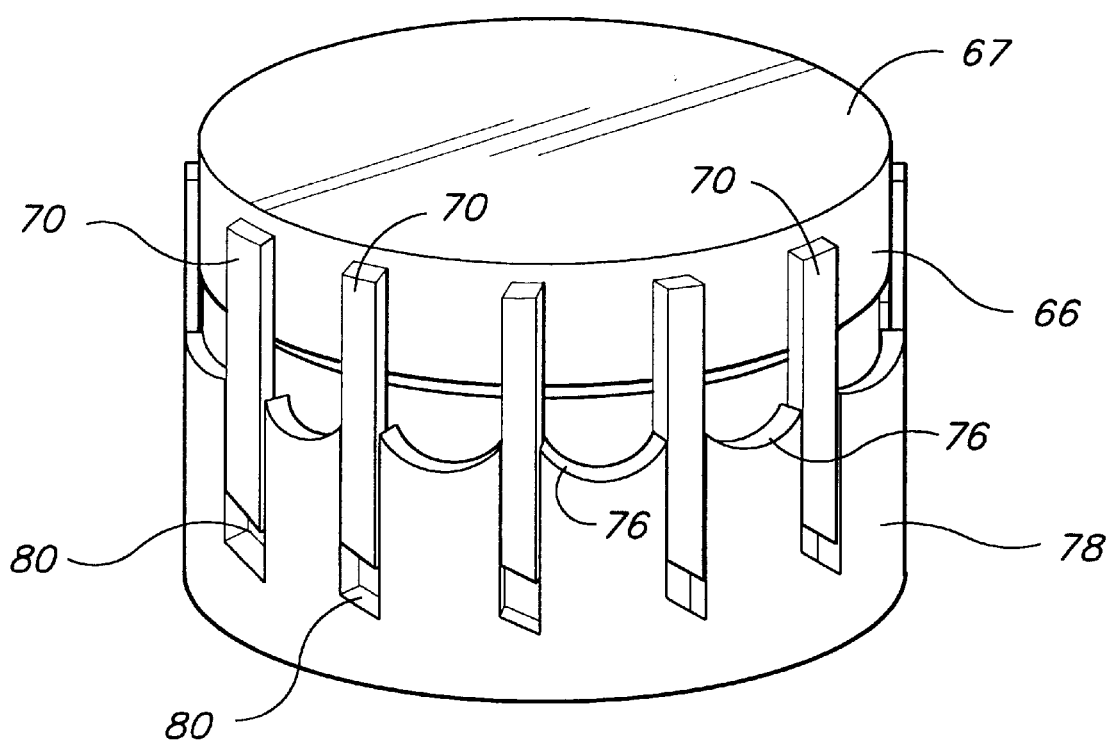
FIG. 8 is a diagrammatical detail view of the closure assembly of the outer casing of FIG. 6 in the open position.
Figure 9:
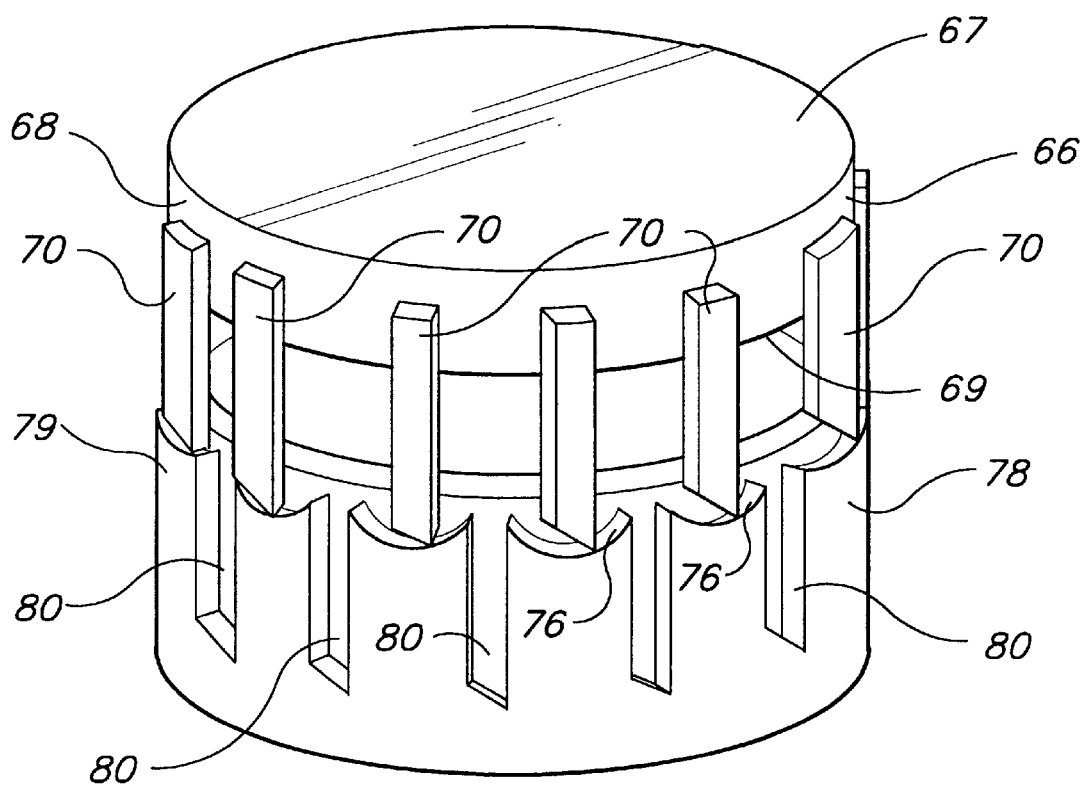
FIG. 9 is a diagrammatical detail view of the closure assembly of the outer casing of FIG. 7 in the closed position.

Referring to FIGS. 8 and 9, there is diagrammatically illustrated closure assembly outer casing 78 as it relates to spaced rotating locker teeth 70 when closure assembly 48 (see FIG. 5) of push button assembly 20 is in the closed position and in the open position, respectively. When spaced rotating locker teeth 70 bear against outer casing locking ridges 76, the assembly is in the closed position as seen in FIG. 9. When spaced rotating locker teeth 70 rest in grooves 80, the assembly is in the open position as seen in FIG. 8. Locking ridges 76 and grooves 80 alternate along the circumference of outer wall 79 of casing 78.

Figure 10:
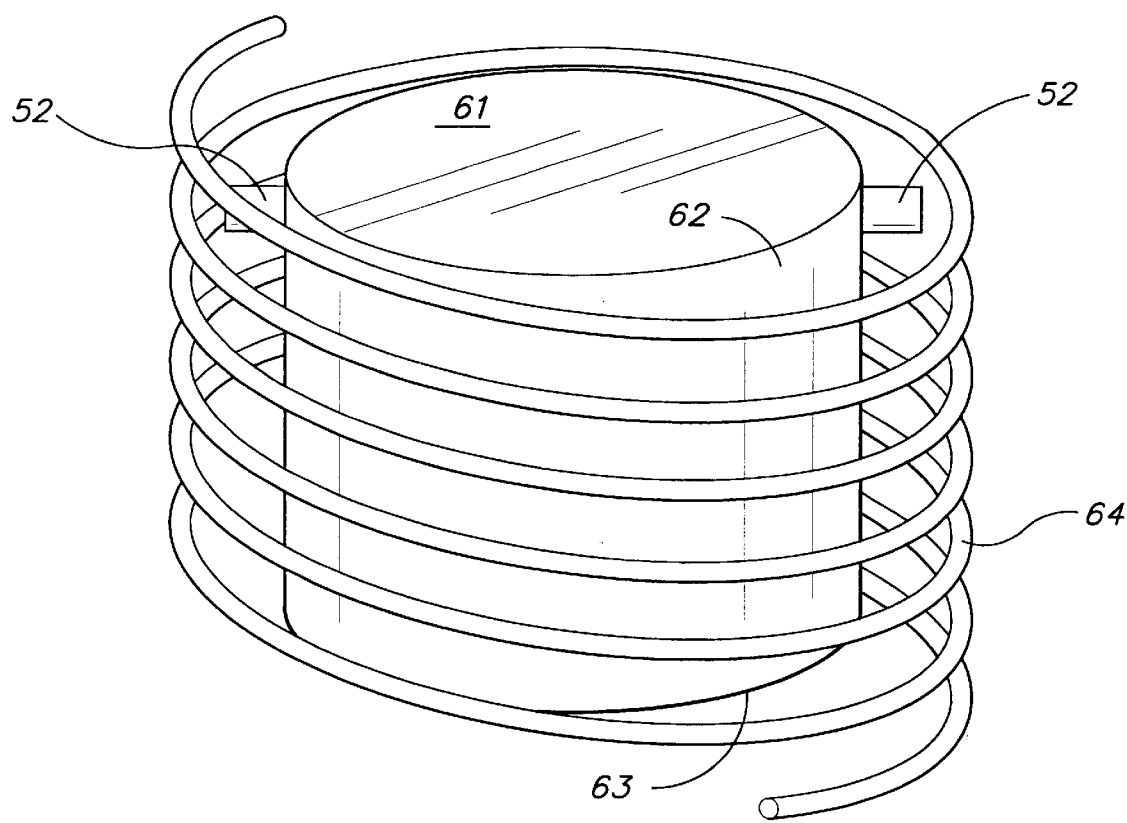
FIG. 10 is a diagrammatical detail view of the inner push rod of FIGS. 6 and 7 with its associated spring.

Referring to FIG. 10, there is shown inner push rod 62 surrounded by inner push rod coil spring 64. Circumferential wires 16 wrap around pulleys 18 (not shown) and are attached diametrically opposed to each other at attachment points 60 (see FIG. 3).

Figure 11:
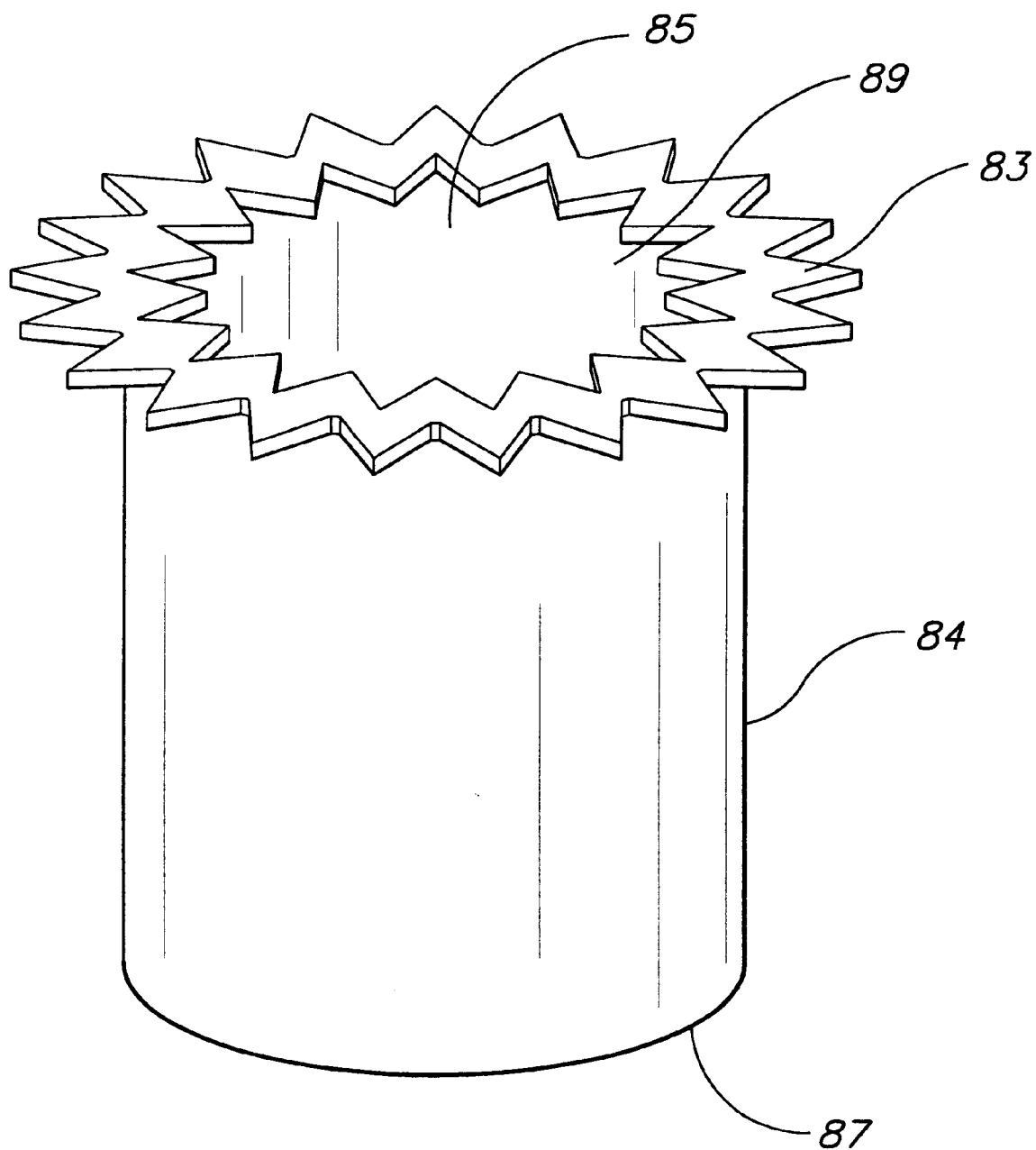
FIG. 11 is a diagrammatical detail view of the outer push rod, with its associated spring, of FIGS. 6 and 7.

Referring to FIG. 11, there is shown hollow cylindrical outer push rod 84 of closure assembly 48, having outer push rod teeth 83 (diagrammatically illustrated) located around its inner end. Outer push rod 84 has a solid outer end wall 87 and an open inner end 89 defining hollow portion 85 configured for receiving the outer end portion 72 of rotating locker 66 (see FIG. 5).

Figure 12:
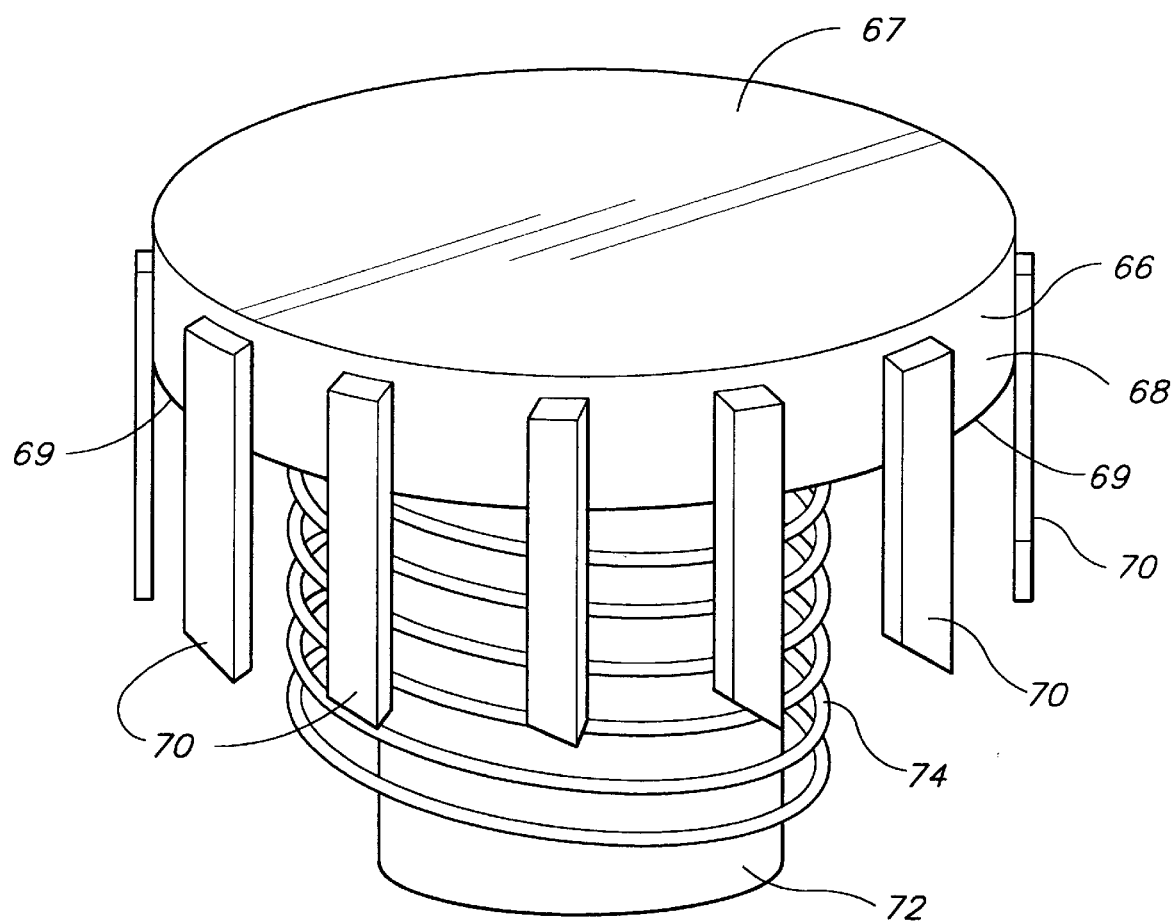
FIG. 12 is a diagrammatical detail view of the rotating locker for the inner push rod of FIGS. 6 and 7.

Referring to FIG. 12, there is shown generally cylindrical rotating locker 66 of closure assembly 48, having an inner end portion 68 of a diameter such that spaced rotating locker teeth 70, mounted thereon, physically interact with closure assembly casing outer wall 79 of push button casing 78 (see FIGS. 8 and 9). An outer portion 72 of rotating locker 66 is of a lesser diameter than the inner portion 68, thereof. Rotating locker outer coil spring 74 is located around the outer portion 72 of rotating locker 66. Rotating locker intermediate wall 69 divides inner portion 68 and outer portion 72. Rotating locker intermediate wall 69 has teeth (not shown) disposed on rotating locker 66 around the perimeter of intermediate wall 69.

Figure 13:
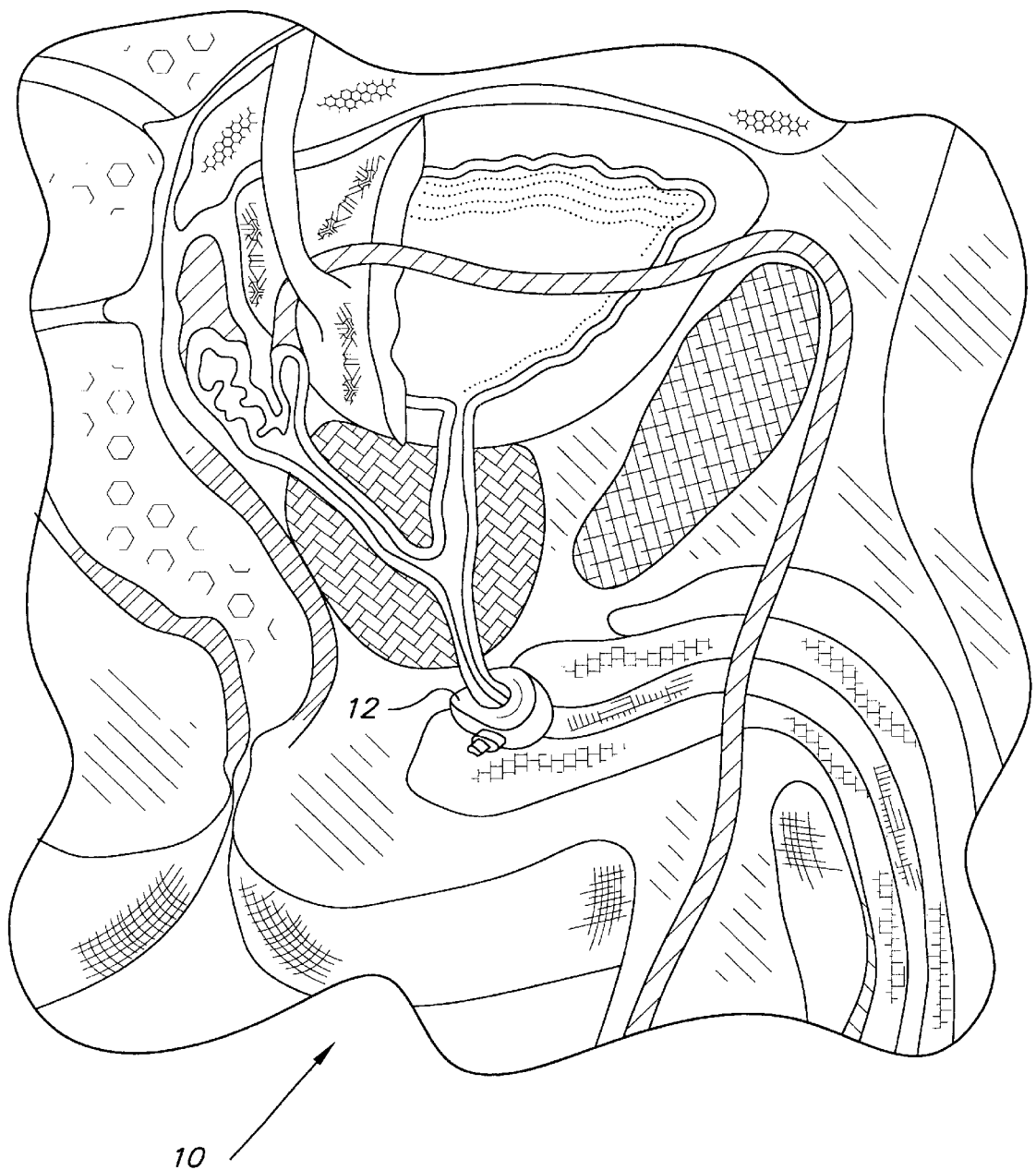
FIG. 13 is an environmental, perspective view of an artificial urinary sphincter inserted in the human body according to the present invention.

Referring to FIG. 13, there is shown a diagrammatical, environmental, perspective view of the artificial urinary sphincter 12 inserted in the human body according to the present invention.

In operation, the artificial sphincter 12 is implanted surgically by sliding the urethra between outer cuff outer end 50 and outer cuff inner end 54 and through inner cuff void space 37 so that the inner cuff 26 surrounds the urethra at its center loosely without putting any pressure on the urethra 38. The outer cuff fixation opening is then snapped over push button base 56 and held in fixation opening groove 55. This is the installed open position of sphincter 12 (See FIG. 3). Its push button assembly is on the skin side interiorly and operable through the skin between an open position and a closed position. Fluid-containing inner cuff walls 28 are on the side of the urethra 38.

When push button 42 is activated by pushing it, the closure assembly 48 will advance and become locked in the closed position. The mechanism is similar to ball point pen refill locking in an open position. It will push the outer cuff inner end 54 and adjacent overlap portion 22 toward the center and will displace the fluid through the chambers 32 concentrically and toward the closed end thereof. This will compress the urethra 38 and close it.

To aid the closure further, as push button 42 is pushed to the closed position, the attached end of wires 16 are pulled over the pulleys 18, respectively, and thus will add radially inward pressure to the inner cuff toward the center of the artificial sphincter. When the sphincter is closed, it will compress the urethra and prevent urine from leaking (See FIG. 4). When the individual desires to urinate, he presses on the push button 42 and thereby the closure assembly 48, and, like a refill of a ball point pen, the closure assembly will retract into the base 56, allowing the fluid in inner cuff 22 to move away from the center as outer cuff 14 moves away from the center. This movement of closure assembly 48 will also release the tension on the wires 16 and allow the inner cuff to move away from the urethra. This will open the urethra and allow urine to flow. The sphincter is closed again by depressing the push button 42.

When outer push rod 84 is pushed, it pushes rotating locker 66 up and its spaced teeth 70 move through grooves 80 on outer wall 79 of push button casing 78. Once spaced teeth 70 have reached above grooves 80, the teeth 70 will lock into spaced locking ridges 76 and will hold inner push rod 62 up, compressing the outer cuff. Spaced locking ridges 76 define grooves 80. This is the closed position of sphincter 12. When outer push rod 52 is pushed again, it pushes the rotating locker 66, and rotates it, so that the grooves 80 and spaced rotating locker teeth 70 align, and the spaced locker teeth 70 slide outward in the grooves 80 under spring pressure, and the rotating locker 66 moves down. Downward movement is aided by inner push rod coil spring 64 and rotating locker coil spring 74. The pressure from inner push rod 62 on the outer cuff 14 is released, opening up the sphincter(See FIG. 6).

The teeth 83 on outer push rod 84, and the teeth on rotating locker intermediate wall 69 engage in such a way that when they are engaged as a result of each push of push button 42 and outer push rod 84, the rotating locker 66 is turned counter clockwise a discrete distance, thereby at one turn aligning spaced locker teeth 70 and grooves 80 between ridges 76, and on the next turn placing spaced locker teeth 70 on ridges 76, thereby alternately locking and unlocking the sphincter. This type of ratcheting and turning mechanism is well known is the retractable pen art as illustrated, for example, in U.S. Pat. No. 3,679,317, issued Jul. 25, 1972 to Ivar G. Larson, hereby incorporated by reference.

Any appropriate materials may be used in the construction of the inventive sphincter, such as titanium and appropriate plastic materials. The outer cuff is of relatively inflexible material, while the inner cuff is of readily flexible material. Nylon or similar cord may be substituted for metal wire in the inventive artificial sphincter.

It is to be understood that the present invention is not limited to the embodiments described above, but encompasses any and all embodiments within the scope of the following claims.

I claim:

1. A generally cylindrical ring shaped artificial urinary sphincter comprising:
    a) an outer cuff having inner and outer ends and an inner and an outer overlap portion near said inner and outer ends, respectively;
    b) an elastic inner cuff encircled by said outer cuff and comprising an outer wall adjacent said outer cuff, and interconnecting, fluid-containing inner cuff chambers having inner ends adapted to be adjacent said urethra, said cuff chambers being partially divided by inner cuff walls extending generally radially from said inner ends to points near said outer wall, said inner cuff having an outer chamber wall defining the beginning of said outer cuff outer overlap portion, and an inner chamber wall at an outer cuff inner end, thus defining a void space allowing the urethra to slide therethrough during cuff installation; and
    c) a push button assembly mounted for relative movement near said outer cuff in said inner overlap portion;
    d) said push button assembly comprising:
        1) an outer base:
        2) a closure assembly; and
        3) a push button;
        4) said outer base being mounted at its inner end to said outer cuff in said overlap portion, and extending outward to receive said push button;
    e) said closure assembly being mounted within said push button assembly and being engaged with said outer cuff inner overlap portion at an inner end and with said push button at an outer end;
    f) said closure assembly of said push button assembly being so constructed that, upon repeated pushing of said push button, said closure assembly alternately presses said inner overlap portion inward so as to compress said inner cuff around said urethra, thereby closing said urethra, and relaxes pressure on said inner overlap portion, thereby relaxing said inner cuff, and thereby opening said urethra.

2. The artificial urinary sphincter of claim 1, wherein said push button assembly comprises a base having a fixation groove around its inner end, said outer overlap portion of said outer cuff having a fixation opening therein which fits within said fixation groove, whereby said artificial sphincter may be installed around said urethra by sliding said urethra between said inner end and said outer end of said outer cuff and then said fixation opening closed over said push button assembly and held in said fixation groove.

3. The artificial urinary sphincter of claim 1 wherein said closure assembly, upon pressing on said push button, alternately extends inward, pressing said inner overlap portion inward so as to compress said inner cuff around said urethra, thereby closing said urethra, and retracts, relaxing pressure on said inner overlap portion, thereby relaxing said inner cuff and opening said urethra.

4. The artificial urinary sphincter of claim 3 further comprising at least one circumferential wire anchored at one end to said outer casing near said fixation opening, and directed around said inner casing to a pulley within said base where it is directed to an attachment point on the inner end of said push button assembly such that upon pushing said push button, said circumferential wire is alternately pulled inward, thus applying radially inward force to said inner cuff, aiding in closure of said sphincter, and relaxed outward, thus releasing inward force and allowing said sphincter to open.

5. The artificial sphincter of claim 4, wherein there are two of said circumferential wires directed over two corresponding pulleys mounted on said base and attached to the inner end of said closure assembly at diametrically opposed attachment points.

6. The artificial sphincter of claim 4 wherein said closure assembly comprises:
    a) an inner push rod;
    b) a rotating locker;
    c) a push button casing: and
    d) an outer push rod;
    e) said inner push rod being cylindrical and having an inner end and an outer end, said inner end bearing on said inner overlap portion of said outer cuff, and said outer end bearing on an inner end of said rotating locker;
    f) said rotating locker being generally cylindrical, having an inner end bearing upon said inner push rod outer end, said rotating locker having a first diameter, and extending outward from said inner end to form an inner portion, said rotating locker having an outer portion having a second diameter that is less than said first diameter, said inner portion and said outer portion defining an intermediate wall therebetween, normal to said rotating locker, said inner portion having spaced teeth mounted to and disposed around said inner portion and extending axially outward from the outer perimeter of said intermediate wall;
    g) said push button casing being a hollow cylinder of about the same diameter as said first rotating locker diameter and having locking ridges spaced around an outer wall and being normal to said casing and forming grooves therebetween, extending lengthwise of said cylinder;

h) said locker spaced teeth physically interacting alternately with said locking ridges and said grooves as said rotating locker rotates on its central axis;

i) said outer rod being cylindrical in shape and hollow from an open inner end to an outer end solid surface bearing on said push button, said outer rod having an inner diameter such as to receive said outer portion of said rotating locker, said inner end having teeth around its circumference and extending outward therefrom;

j) said intermediate wall of said rotating-locker having teeth extending around its surface so sized and shaped as to interact with said teeth of said outer push rod in a manner so as to turn said rotating locker a discreet distance upon each engagement with said teeth in a ratcheting manner;

whereby, upon pushing said push button, said outer rod is displaced so as to bear its inner end teeth against said rotating locker intermediate wall teeth, thereby displacing said rotating locker inward and rotating said locker a discreet amount in a ratcheting manner, and thereby lifting and rotating said spaced teeth depending from said first portion of said rotating locker from said casing grooves to said casing locking ridges ultimately displacing said inner rod, which bears on said inner overlap portion of said outer cuff, said cuff being displaced to a closed position, and, upon said push button being pushed again, said rotating locker and said spaced teeth are rotated another equal discreet amount allowing said spaced teeth to slide into said casing grooves, thus releasing pressure on said inner rod and thereby allowing said inner overlap portion of said outer cuff to relax and displace outward, thus assuming an open position.

7. The artificial urinary sphincter of claim 6, further comprising an inner coil spring surrounding and coaxial with said inner push rod and bearing at its inner end against said inner overlap portion of said outer casing, and bearing at its outer end against said inner end of said rotating locker, thereby forcing said rotating locker spaced teeth to being either bearing against said casing locking ridges or sliding into said casing grooves.

8. The artificial urinary sphincter of claim 7, further comprising an outer coil spring located around and coaxial with said outer portion of said rotating locker and bearing against said intermediate wall and said inner end of said outer push rod, thereby forcing said outer rod outward, said push button bearing against same to a rest position when said outer cuff is in an open condition, and assisting in forcing said rotating locker upward when changing between alternate open and closed conditions.

9. The artificial urinary sphincter of claim 8, further comprising an outer push rod cuff mounted around said outer push rod and extending from the outer surface thereof to an inner wall of said closure assembly casing and mounted outward from said outer push rod angled teeth.

10. An artificial urinary sphincter implant comprising:

a) means adapted for surrounding a urethra for alternately applying radially inward force on said urethra, accomplishing closure, and relaxing said radially inward force to allow opening thereof; and b) said means adapted for surrounding said urethra having actuating means for alternately compressing and relaxing said surrounding means;

wherein pushing said actuating means a first time applies said radially inward force, whereby the urethra is closed, thus maintaining continence of the user, and wherein pushing said actuating means a second time relaxes said radially inward force, whereby the urethra is opened to allow flow of urine.

11. The artificial urinary sphincter implant of claim 10, said actuating means comprising a push button, a push button casing, and a closure assembly.

12. The artificial urinary sphincter implant of claim 11, said means surrounding said urethra having interconnecting fluid-containing compartments.

13. The artificial urinary sphincter implant of claim 12, said fluid-containing compartments having overlapping outer cuff means actuated by said closure assembly means for alternately applying radial inward pressure on said fluid-containing compartment means. and relaxing inward pressure on said fluid-containing means.

14. The artificial urinary sphincter implant of claim 12, said means surrounding said urethra having circumferential wire means for alternately applying inward radial pressure to said fluid-containing compartment means and releasing radial pressure to said fluid-containing compartment means.

* * * * *